(12) United States Patent
Holman et al.

(10) Patent No.: US 11,819,244 B2
(45) Date of Patent: Nov. 21, 2023

(54) SURGICAL DEVICE FOR TREATMENT OF ENDOMETRIOSIS

(71) Applicant: GYRUS ACMI, INC., Southborough, MA (US)

(72) Inventors: Thomas J. Holman, Princeton, MN (US); Nikhil M. Murdeshwar, Maple Grove, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 268 days.

(21) Appl. No.: 17/099,197

(22) Filed: Nov. 16, 2020

(65) Prior Publication Data

US 2021/0153899 A1 May 27, 2021

Related U.S. Application Data

(60) Provisional application No. 62/941,079, filed on Nov. 27, 2019.

(51) Int. Cl.
*A61B 17/32* (2006.01)
*A61B 17/42* (2006.01)
*A61B 17/00* (2006.01)

(52) U.S. Cl.
CPC .. *A61B 17/4241* (2013.01); *A61B 17/320016* (2013.01); *A61B 2017/00867* (2013.01);
(Continued)

(58) Field of Classification Search
CPC .. A61B 17/320016; A61B 2017/00353; A61B 2017/00867; A61B 2017/32004;
(Continued)

(56) References Cited

U.S. PATENT DOCUMENTS

| 4,499,899 A | 2/1985 | Lyons, III |
| 5,772,597 A | 6/1998 | Goldberger et al. |

(Continued)

FOREIGN PATENT DOCUMENTS

| CN | 112932688 A | 6/2021 |
| WO | WO-2014164643 A1 | 10/2014 |
| WO | WO-2017007851 A1 | 1/2017 |

OTHER PUBLICATIONS

"European Application Serial No. 20209102.1, Extended European Search Report dated Apr. 7, 2021", 4 pgs.

(Continued)

*Primary Examiner* — Diane D Yabut
*Assistant Examiner* — Christian D. Knauss
(74) *Attorney, Agent, or Firm* — Schwegman Lundberg & Woessner, P.A.

(57) ABSTRACT

Surgical instruments and methods are disclosed including a tissue removal tool for treatment of endometrial tissue on a background tissue of a patient. The tissue removal tool can optionally comprise a graspable portion, a shaft and an end effector. The shaft can be coupled to the graspable portion. The shaft can have a proximal portion and a distal portion and can be configured to access an anatomic location of the endometrial tissue. The end effector can be coupled to the distal portion of the shaft. The end effector can be configured to lift the endometrial tissue relative to the background tissue to a lifted position. The end effector can be configured to cut the endometrial tissue from the background tissue with the endometrial tissue in the lifted position.

16 Claims, 6 Drawing Sheets

(52) U.S. Cl.
CPC ............. *A61B 2017/320052* (2013.01); *A61B 2017/320075* (2017.08); *A61B 2017/4216* (2013.01); *A61B 2217/005* (2013.01)

(58) Field of Classification Search
CPC ....... A61B 2017/320052; A61B 2017/320075; A61B 2017/4216; A61B 2217/005; A61B 17/221; A61B 17/320783; A61B 17/42; A61B 2017/2212; A61B 2017/2215; A61B 2017/2217; A61B 2017/320791; A61B 1/303; A61B 1/313
See application file for complete search history.

(56) References Cited

U.S. PATENT DOCUMENTS

| | | | |
|---|---|---|---|
| 6,068,603 A | 5/2000 | Suzuki | |
| 6,213,995 B1 | 4/2001 | Steen et al. | |
| 7,651,503 B1* | 1/2010 | Coe ..................... | A61N 1/056 606/108 |
| 8,435,237 B2 | 5/2013 | Bahney | |
| 9,851,741 B2 | 12/2017 | Lamser et al. | |
| 2004/0082969 A1* | 4/2004 | Kerr ................... | A61B 17/0218 606/205 |
| 2004/0158263 A1* | 8/2004 | McAlister ............ | A61B 17/068 606/139 |
| 2008/0125663 A1 | 5/2008 | Golijanin | |
| 2012/0071812 A1 | 3/2012 | Mitelberg et al. | |
| 2013/0211321 A1 | 8/2013 | Dubois et al. | |
| 2016/0045277 A1 | 2/2016 | Lin et al. | |
| 2016/0157920 A1 | 6/2016 | Vayser et al. | |
| 2016/0374658 A1* | 12/2016 | Piskun ............. | A61B 17/00234 600/204 |
| 2018/0028217 A1* | 2/2018 | Hassidov ........... | A61B 18/1492 |
| 2019/0013371 A1 | 5/2019 | Blus et al. | |
| 2019/0282254 A1 | 9/2019 | Fiksen et al. | |
| 2019/0298321 A1* | 10/2019 | Intintoli ............. | A61B 1/00094 |
| 2019/0321093 A1 | 10/2019 | Greeley et al. | |
| 2021/0153731 A1 | 5/2021 | Murdeshwar | |

OTHER PUBLICATIONS

"European Application Serial No. 20209102.1, Communication Pursuant to Article 94(3) EPC dated Apr. 12, 2021", 6 pgs.

U.S. Appl. No. 17/100,025, filed Nov. 20, 2020, Surgical Instruments With Integrated Lighting Systems.

"Chinese Application Serial No. 202011351214.5, Voluntary Amendment filed Aug. 1, 2022", w English claims, 6 pgs.

"European Application Serial No. 20209102.1, Response filed Jul. 20, 2021 to Communication Pursuant to Article 94(3) EPC dated Apr. 12, 2021", w/ English Claims, 7 pgs.

"European Application Serial No. 20209104.7, Extended European Search Report, dated Apr. 7, 2021", 8 pgs.

* cited by examiner

SURGICAL DEVICE FOR TREATMENT OF ENDOMETRIOSIS

CROSS-REFERENCE TO RELATED APPLICATION

This application claims the benefit of priority to U.S. Provisional Patent Application Ser. No. 62/941,079, filed Nov. 27, 2019, the contents of which are incorporated herein in their entirety.

TECHNICAL FIELD

This document pertains generally, but not by way of limitation, to surgical devices, and more particularly, to a device having a tissue removal tool for removing endometrial tissue.

BACKGROUND

Many surgical devices have an end effector. Indeed, an end effector is often used for surgical procedures such as laparoscopic procedures and endoscopic procedures. End effectors are generally used to manipulate, engage, grasp, or otherwise interact with anatomical features, such as a vessel or other tissue.

Endometriosis is a condition where tissue that normally lines the inside of the uterus, the endometrium, grows outside the uterus. Often, endometriosis occurs in and around the abdomen, such as near the ovaries, fallopian tubes, and other tissue lining of the abdomen. In some cases, endometrial tissue can spread beyond tissue of the reproductive system to the urinary tract, for example. Endometriosis can include shallow endometrial tissue in and around these areas, and/or deeper endometrial tissue. The condition can be particularly painful as the endometrial tissue outside the uterus continues to behave in the manner of endometrial tissue within the uterus during the menstrual cycle by thickening, breaking-down and bleeding.

Overview

Because of the variety of locations for endometrial tissue growth and the variety of thicknesses and behaviors of endometrial tissue, there is a need for improved treatment of endometriosis, for example, by improvement in the surgical devices, and in particular, the end effector used to treat endometrial tissue.

The present inventors have recognized, among other things, that the foregoing problems can be addressed by tissue removal tools for endoscopic or laparoscopic treatment of endometrial tissue as disclosed herein. More particularly, the present inventors have recognized various tissue removal tools that can lift (for example, at least partially separate, at least partially delineate) endometrial tissue from background tissue prior to cutting the endometrial tissue.

Example 1 is a tissue removal tool for treatment of endometrial tissue on a background tissue of a patient. The tissue removal tool can optionally comprise a graspable portion, a shaft and an end effector. The shaft can be coupled to the graspable portion. The shaft can have a proximal portion and a distal portion and can be configured to access an anatomic location of the endometrial tissue. The end effector can be coupled to the distal portion of the shaft. The end effector can be configured to lift the endometrial tissue relative to the background tissue to a lifted position. The end effector can be configured to cut the endometrial tissue from the background tissue with the endometrial tissue in the lifted position.

Example 2 is the tissue removal tool of Example 1, wherein the end effector can be movable relative to the shaft to interface with the background tissue about the endometrial tissue.

Example 3 is the tissue removal tool of Example 2, wherein the end effector can be movable about at least an axis transverse to a longitudinal axis of the shaft.

Example 4 is the tissue removal tool of any one or combination of Examples 1-3, wherein the end effector can be configured to cut the endometrial tissue from the background tissue by receiving the endometrial tissue within a cavity of the end effector.

Example 5 is the tissue removal tool of any one or combination of Examples 1-4, wherein the end effector can be configured to cut in a plane that is substantially parallel with a surface of at least one of the background tissue or the endometrial tissue.

Example 6 is the tissue removal tool of any one or combination of Examples 1-5, wherein the end effector can be configured as a suction port to lift the endometrial tissue by gathering.

Example 7 is the tissue removal tool of any one or combination of Examples 1-5, wherein the end effector can be configured as a shape memory element to lift the endometrial tissue by grasping.

Example 8 is the tissue removal tool of any one or combination of Examples 1-7, wherein the end effector can be configured to cut the endometrial tissue in a direction that can be transverse to a direction in which the end effector is configured to lift the endometrial tissue.

Example 9 is an end effector of a tissue removal tool for treatment of endometrial tissue on a background tissue of a patient. The end effector can optionally comprise an actuator and a blade. The actuator can be configured to gather the endometrial tissue relative to the background tissue. The blade can be configured to cut the endometrial tissue with the endometrial tissue gathered from the background tissue. The blade can cut in a plane that is in a range of between about 45 degrees and about 135 degrees, inclusive, to a direction in which the actuator gathers the endometrial tissue.

Example 10 is the end effector of Example 9, wherein the actuator can comprise a shape memory element to gather the endometrial tissue.

Example 11 is the end effector of Example 9, wherein the actuator can comprise a vacuum configured to gather the endometrial tissue.

Example 12 is the end effector of any one or combination of Examples 9-11, further optionally comprising a shaft of the cutting tool, wherein the end effector can be movable relative to the shaft to interface with the background tissue about the endometrial tissue.

Example 13 is the end effector of any one or combination of Examples 9-12, wherein the blade can be configured to cut the endometrial tissue from the background tissue in a direction that can be substantially transverse to the direction in which the actuator gathers the endometrial tissue with the endometrial tissue received within a cavity of the end effector.

Example 14 is the end effector of any one or combination of Examples 9-13, wherein the tissue cutting element can be configured to cut the endometrial tissue in a direction that can be substantially transverse to a direction the actuator is configured to lift the endometrial tissue.

Example 15 is the end effector of any one or combination of Examples 9-14, wherein the actuator can be configured to gather the endometrial tissue in a direction that can be in a range of between about 45 degrees and about 135 degrees, inclusive, to one of the background tissue or a longitudinal axis of the end effector.

Example 16 is a method of treating endometrial tissue at an anatomical location. The method can optionally comprise: guiding an end effector to the anatomical location; lifting the endometrial tissue relative to a background tissue with the end effector; and cutting the endometrial tissue from the background tissue with the end effector and with the endometrial tissue lifted from the background tissue.

Example 17 is the method of Example 16, wherein cutting the endometrial tissue can be in a direction transverse to a direction of the lifting the endometrial tissue.

Example 18 is the method of any one or combination of Examples 16-17, optionally further comprising manipulating the end effector to interface with the background tissue.

Example 19 is the method of any one or combination of Examples 16-18, wherein lifting the endometrial tissue can comprise gathering the endometrial tissue with suction or a shape memory element.

Example 20 is the method of any one or combination of Examples 16-18, wherein lifting the endometrial tissue can comprise grasping the endometrial tissue with a shape memory element.

Example 21 is any one or any combination of the elements of Examples 1-20.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

DETAILED DESCRIPTION

The present disclosure is directed to a surgical device such as a cutting tool that can allow a surgeon to operate an end effector to perform such cutting. It is contemplated that the terms "lift" or "lifting" as used herein does not connote use of movement in a reference direction such as a gravitational direction. Rather, the terms "lift" or "lifting" as used herein means to manipulate a position such as to at least partially separate or at least partially delineate a target tissue such as endometrial tissue from a background tissue. As further disclosed herein "lift" or "lifting" can be performed by grasping, gathering, pulling or otherwise manipulating a position of the target tissue (e.g., endometrial tissue) as further discussed herein. The "lift" or "lifting" need not be in a direction transverse to background tissue. Rather, the "lift" or "lifting" can be in any direction such as, but not limited to between 45 and 135 degrees, inclusive of a longitudinal axis of the end effector or of a surface of the background tissue. The "lift" or "lifting" can be performed so as to least partially separate or at least partially delineate the target tissue such as endometrial tissue from the background tissue.

In this disclosure, relative terms, such as, for example, "about", "generally", or "substantially" are used to indicate a possible variation of ±10% in a stated numeric value or within ±10° of the numeric value.

Figure 1:
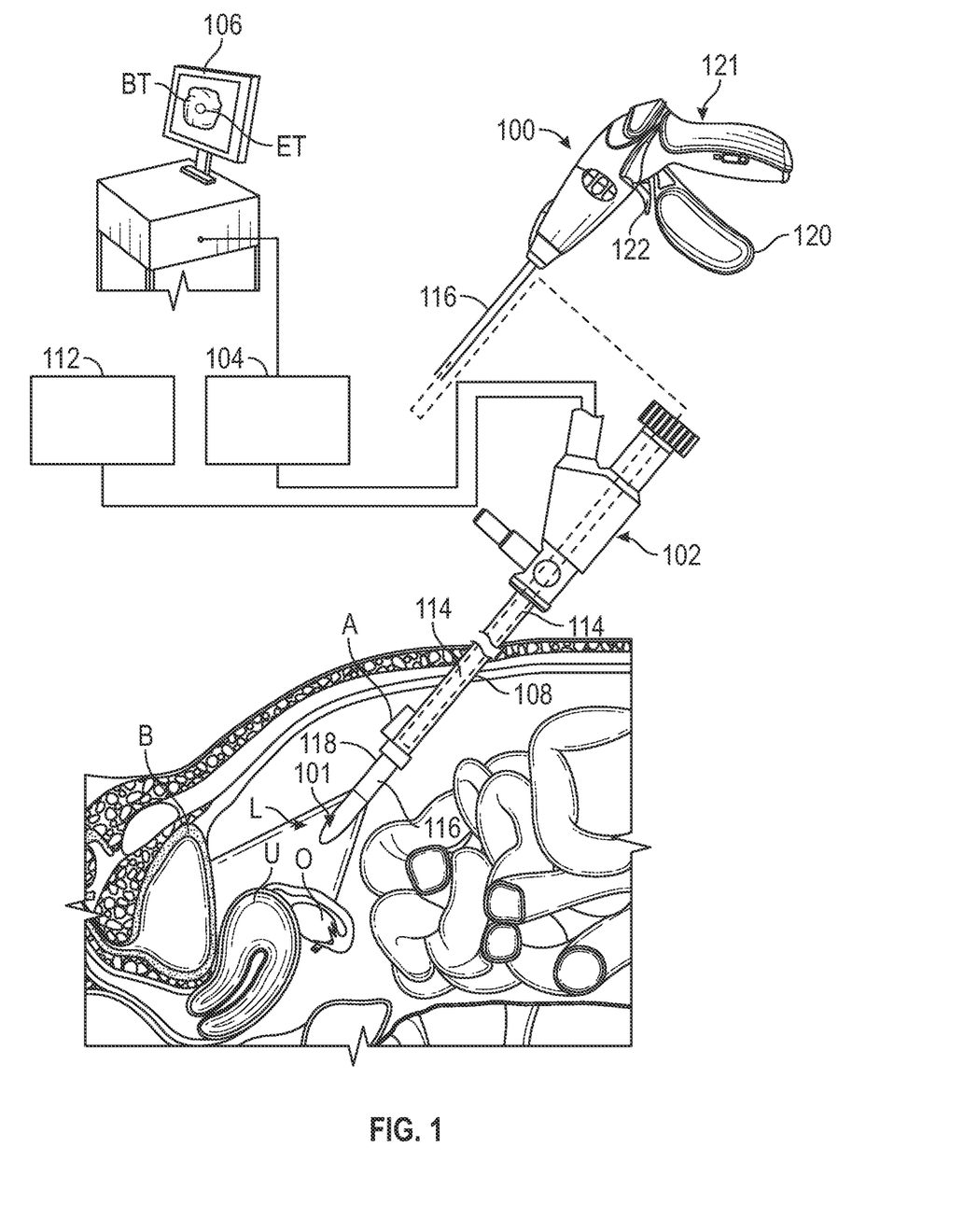
FIG. 1 is a schematic view of a first example of a tissue removal tool that can be used in a laparoscopic or open procedure according to the present application.

FIG. 1 is a schematic diagram of a laparoscopic surgical procedure being performed with a tissue removal tool 100. Elements of FIG. 1 are not drawn to scale for illustrative purposes. The procedure of FIG. 1 is illustrated as a laparoscopic procedure but the tissue removal tool 100 alternatively can be utilized in an open or endoscopic procedure, for example.

The surgical procedure of FIG. 1 can be performed to remove or otherwise abate target tissue such as endometrial tissue that is diseased or invasive. FIG. 1 illustrates a surgical procedure being performed to remove endometrial tissue from the cavity of abdomen A that has grown outside of uterus U. However, the instruments and methods of the present application can be used to perform other procedures, such as to remove target tissue such as cysts, polyps, abscesses, fibroids, tumors, lymph node tissue, etc.

FIG. 1 illustrates an operating room environment where the tissue removal tool 100 can be used with a laparoscope 102 and can be coupled to or used in conjunction with a camera 104 and display 106. The patient can be appropriately anesthetized during the procedure. As shown in FIG. 1, an incision 108 can be made in abdomen A of the patient. The incision 108 can be a minimally invasive incision sized to receive the laparoscope 102 and cutting tool 100. However, the incision 108 can alternatively be an incision having a sufficient length to form a portal for performing an open procedure using the cutting tool 100.

The tissue removal tool 100 can be inserted into the incision 108. The tissue cutting device 100 can be coupled to the camera 104 for viewing tissue within abdomen A of the patient internal to incision 108. Camera 104 can be configured to be used in conjunction with various visualization techniques such as, but not limited to UV, contrast, dye, etc. to better visualize the target tissue (e.g., the endometrial tissue). The tissue of uterus U, bladder B, ovaries O and other locations and organs, such as fallopian tubes and the rectum, can be identified using the camera 104, for example.

The tissue removal tool 100 can also be coupled to or otherwise used with a device 112 such as a vacuum or generator according to some examples for purposes discussed subsequently. The tissue cutting device 100 can include one or more passages 114 that extends through incision 108 to allow access to internal tissue of the patient from outside the patient.

The tissue removal tool 100 having an end effector 101 (as further illustrated and described) can be inserted into incision 108. For example, the end effector 101 of the tissue removal tool 100 can be inserted into one of the one or more passages 114 of the laparoscope 102. Specifically, a shaft 116 of the tissue removal tool 100 can be inserted through the one of the one or more passages 114 such that the end effector 101 protrudes from the one of the one or more passages 114 and is located inside abdomen A.

A light emitting device 118 can also be positioned within abdomen A. Light can be generated by a light source to be emitted by the light emitting device 118 into the cavity abdomen A. The light source and/or the light emitting device 118 can be attached to the surgical instrument. The light can be white light or UV light to visually aid viewing of tissue. The light can additionally be light of a wavelength sufficient to energize, e.g., fluoresce, dye, such as near-infrared (NIR) light. NIR light can be used to energize indocyanine green in endometriosis surgeries, for example. Further details regarding the construction of the light emitting device 118 can be found in co-filed U.S. Provisional Patent Application No. 62/940,328, entitled "SURGICAL INSTRUMENTS WITH INTEGRATED LIGHTING SYSTEMS", filed Nov. 26, 2019, the specification of which is incorporated by reference in its entirety.

The target tissue (e.g., here endometrial tissue indicated as "ET") can be identified or differentiated from background tissue "BT" by the light and/or various known methods including dye, contrast, etc. and can be treated with the tissue removal tool 100 as further discussed herein. For example, light L emitted within the abdomen A can pass around the end effector 101 to illuminate tissue on ovary O. The tissue removal tool 100 can have a graspable portion 121 in addition to the shaft 116. The shaft 116 can be coupled to the graspable portion at a proximal portion thereof. The end effector 101 can be coupled to a distal portion of the shaft 116. The tissue removal tool 100 can also include a first actuator 120 such as a lever, trigger, button or valve operable to lift the endometrial tissue ET and a second actuator 122 such as a trigger or button operable to cut the target tissue and remove the target tissue from abdomen A. For example, the first actuator 120 can be utilized to couple the device 112 comprising the vacuum with the end effector 101 as discussed in reference to FIGS. 2A and 2B. According to other examples, the first actuator 120 can allow electromagnetic energy in the form of current from the device 112 comprising the generator to directed to the end effector 101 to provide for shape memory grasping or other type of manipulation of the tissue including the endometrial tissue ET as discussed in reference to FIGS. 3A and 3B.

Figure 2A:
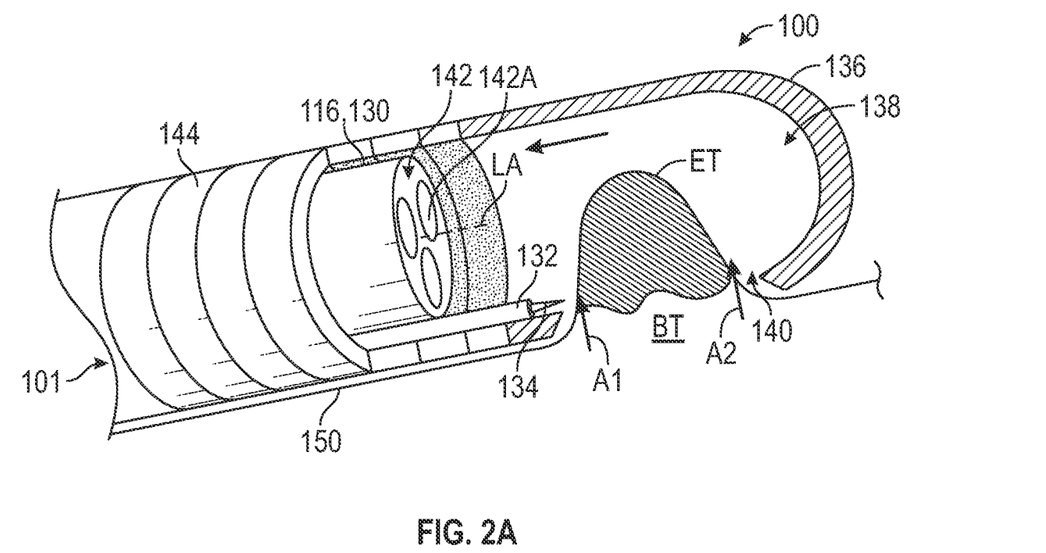
FIG. 2A is a side view, in partial cross-section, illustrating a first end effector of the tissue removal tool of FIG. 1 configured for removing endometrial tissue from a background tissue with a blade thereof in a first retracted position according to an example of the present application.
Figure 2B:
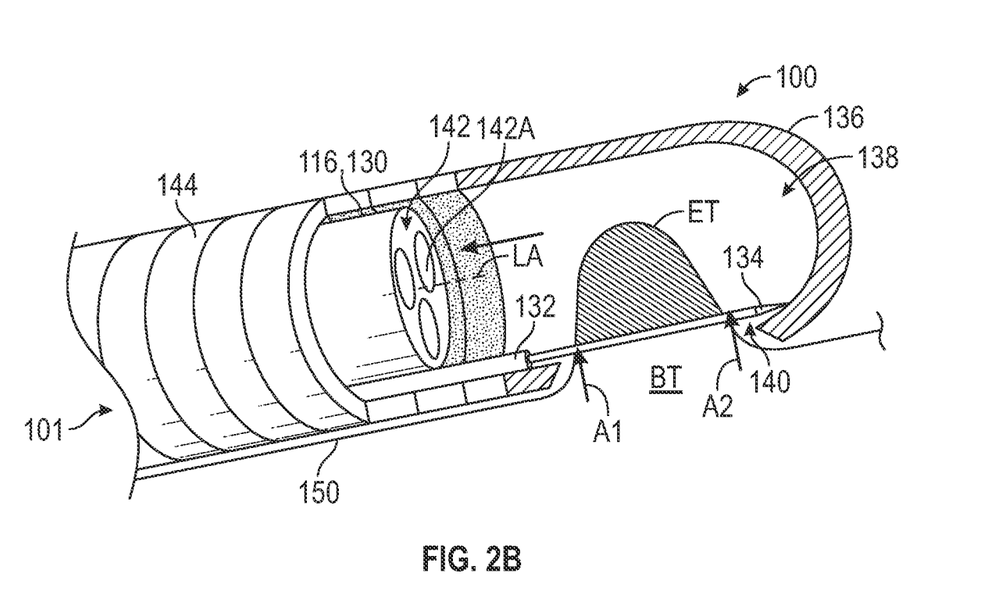
FIG. 2B is another side view, in partial cross-section of device of FIG. 2A with a blade in a second extended position to cut and remove the endometrial tissue from the background tissue according to an example of the present application.

FIGS. 2A and 2B show the tissue removal tool 100, and in particular, a distal portion 130 of the shaft 116 and the end effector 101. The end effector 101 can include a sheath 132, a blade 134, a housing 136, a cavity 138 and a suction port 140. The shaft 116 can include one or more passageways 142 including a suction passageway 142A.

As shown in FIG. 2A, the sheath 132 can be positioned within the housing 136 adjacent the shaft 116. The sheath 132 can be configured to house the blade 134 in the retracted position shown in FIG. 2A. The blade 134 can be positioned adjacent but spaced slightly such as in a direction (indicated with arrows A1 and A2) transverse to a longitudinal axis LA of the shaft 116 from the housing 136 and the suction port 140, for example. The blade 134 can be movable within the cavity 138 from the retracted position of FIG. 2A to the extended position of FIG. 2B. The cavity 138 can be defined by the housing 136 and can be configured to receive endometrial tissue ET (indicated with hatching) therein in addition to other components including the sheath 132, the blade 134 and the distal portion 130. The housing 136 can also define the suction port 140, which can comprise an aperture or apertures extending through the housing 136 and providing a passage from an exterior of the end effector 101 to the interior the cavity 138. The suction port 140 can be configured to receive the endometrial tissue ET and allow for passage of at least a portion of the endometrial tissue ET into the cavity 138.

In some examples, the end effector 101 can have a flexible or semi-compliant portion 144. The portion 144 can be configured to be movable relative to the shaft 116. Thus, the end effector 101 can be movable relative to the shaft 116 to interface (or abut)) with the background tissue BT that is adjacent to the endometrial tissue ET. Put another way, the portion 144 can be configured to allow the end effector 101 to be compliant with the background tissue BT to seat thereon, according to some examples. Put another way, the portion 144 can allow the end effector 101 to be movable about at least an axis (generally corresponding with the arrows A1 and A2) transverse to the longitudinal axis LA of the shaft 116.

As shown in FIG. 2A, the end effector 101 can be configured to gather the endometrial tissue ET relative to the background tissue BT to a lifted position by application of suction from the device 112 (FIG. 1) via the suction passageway 140A. Suction passageway 140A can communicate with the cavity 138 to provide a low pressure such as a vacuum to the cavity 138 and the suction port 140. The suction provided to the cavity 138 and the suction port 140 can be configured to lift the endometrial tissue ET by gathering it within and into the suction port 140 and/or cavity 138 as shown in FIG. 2A.

Turning to FIG. 2B, the blade 134 is shown in the extended tissue cutting position to cut and remove the endometrial tissue ET from the background tissue BT. This can be done while the suction discussed in FIG. 2A is applied. Thus, the end effector 101 can be configured to cut the endometrial tissue ET from the background tissue BT with the endometrial tissue in the lifted position by receiving the endometrial tissue within the cavity 138 as facilitated by the suction as shown in FIG. 2B. The end effector 101 can be configured to cut in a plane (co-planar with blade 134) that is substantially parallel with a surface 150 of at least one of the background tissue BT or the endometrial tissue ET, for example. Such cutting arrangement can be facilitated by the portion 144 previously discussed, for example. As shown in FIG. 2B, the end effector 101 can be configured to cut the endometrial tissue ET in a direction transverse to a direction (corresponding to the direction of arrows A1 and A2) in which the end effector 101 is configured to lift the endometrial tissue ET.

It should be noted that although a blade (mechanical facilitated cutting) is illustrated in performing the cutting of FIG. 2B, it is contemplated in other examples that the cutting can be performed in an energized manner (e.g., electromagnetic, laser or another configuration or modality as known in the art). Similarly, rather than cutting parallel with the longitudinal axis LA, the blade can be configured to cut transverse to the longitudinal axis or in another direction or can be rotatable such as around the longitudinal axis LA or in another direction about another axis. According to other examples, the tissue removal tool can utilize the one or more passages 142 for various purposes such as to suction the cut endometrial tissue ET away from the cutting location. For example, the one or more passages 142 additional extraction capabilities and/or tools. For example, the one or more passages 142 can be used to morcellate or macerate tissue. According to one example, an auger type device (not shown) can reside in one of the one or more passages 142 and can extend out of one of the ports thereof to remove tissue. The one or more passages can be utilized for other purposes such as to freeze or cauterize the background tissue BT after cutting, for example.

Figure 3A:
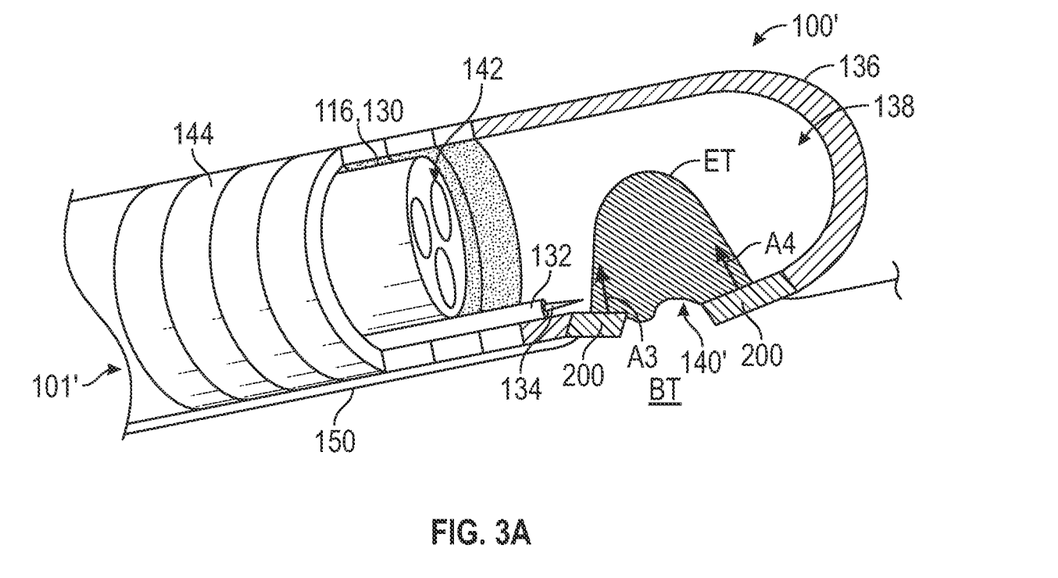
FIG. 3A is a side view, in partial in cross-section, illustrating a second end effector of the tissue removal tool of FIG. 1 configured for removing endometrial tissue from a background tissue with a blade thereof in the first retracted position according to an example of the present application.
Figure 3B:
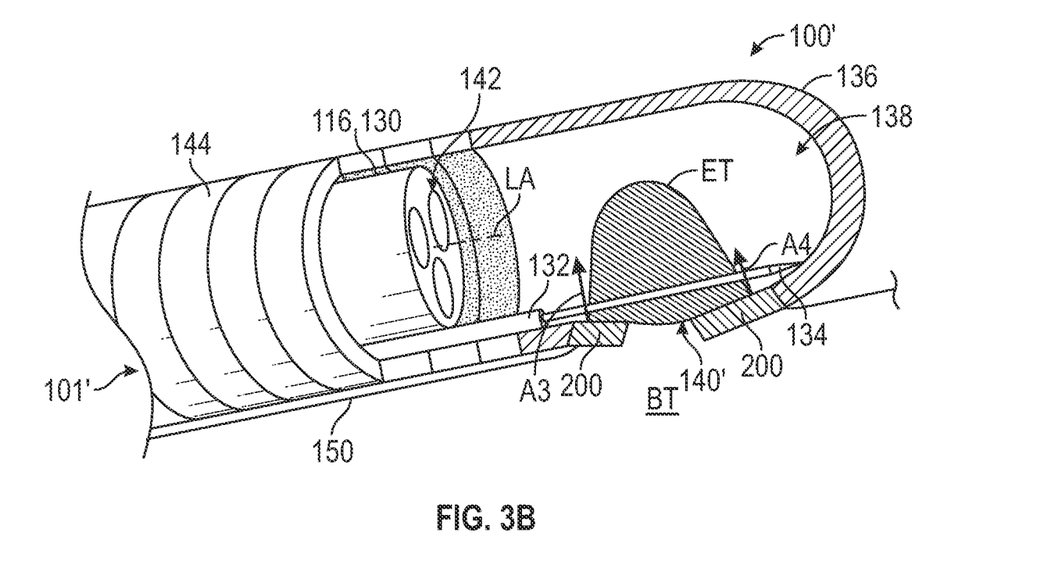
FIG. 3B is another side view, in partial cross-section of the device of FIG. 3A with a blade in a second extended position to cut and remove the endometrial tissue from the background tissue according to an example of the present application.

FIGS. 3A and 3B show another example of a tissue removal tool 100'. The tissue removal tool 100' differs from the tissue removal tool 100 of FIGS. 2A and 2B in that an end effector 101' includes a shape memory element 200 configured to lift the endometrial tissue ET by grasping and gathering as illustrated in FIG. 3A. Thus, the port 140' of FIG. 3A does not comprise a suction port formed by the housing 136 but is a receptacle formed at least in part by the shape memory element 200 and used in conjunction with the shape memory element 200 to receive the endometrial tissue ET.

In other respects, the tissue removal tool 100' can be the same as the tissue removal tool 100 of FIGS. 2A and 2B. Thus, the end effector 101' can include the sheath 132, the blade 134, the housing 136 and the cavity 138 as previously described. The shaft 116 can include the one or more passageways 142.

As shown in FIG. 3A, the end effector 101' can be configured to lift the endometrial tissue ET relative to the background tissue BT to a lifted position by application of current from the device 112 (FIG. 1) to cause the shape memory element 200 to actuate (e.g., extend, change shape, curl, etc.). Alternatively, the shape memory element 200 can change shape on its own due to a body temperature of the patient, for example. Although the shape memory element 200 is described in the singular it can comprise a plurality of elements such as fingers, hooks, jaws or the like. Further examples of shape memory elements 300, 400 and 500 that can be utilized with the end effectors described herein are illustrated in FIGS. 4A-6B. According to some examples, the shape memory element 200 can be a nitinol material or another biologically stable shape memory alloy or shape memory polymer as known in the art. According to some examples, the shape memory element 200 can be configured with one or more edges that can be become sharp (or serrated) and capable of cutting the endometrial tissue ET when actuated. According to some examples, the shape memory element 200 can include an electrically conductive element to facilitate removal (e.g., monopolar or bipolar cutting). Alternatively, cutting by the shape memory element 200, may be non-conductive as discussed previously facilitated by serrated edge(s), sharpened edge(s) or another feature of the shape memory element 200 or a dedicated blade as in the previously illustrated examples.

As shown in FIG. 3B, the blade 134 is shown in the extended tissue cutting position to cut and remove the endometrial tissue ET from the background tissue BT. This can be done while the shape memory element 200 is actuated to lift the endometrial tissue ET. Thus, the end effector 101' can be configured to cut the endometrial tissue ET from the background tissue BT with the endometrial tissue in the lifted position as shown in FIG. 3B. As illustrated in FIG. 3B, the end effector 101' can be configured to cut the endometrial tissue ET from the background tissue BT by receiving the endometrial tissue within the cavity 138 as facilitated by the shape memory element 200. The end effector 101' can be configured to cut in a plane (co-planar with blade 134) that is substantially parallel with a surface 150 of at least one of the background tissue BT or the endometrial tissue ET, for example. Such cutting arrangement can be facilitated by the portion 144 previously discussed, for example. As shown in FIG. 3B, the end effector 101' can be configured to cut the endometrial tissue ET in a direction that is in a range of between about 45 degrees and about 135 degrees, inclusive, to a direction (corresponding to the direction of arrows A3 and A4 of FIG. 3A) in which the end effector 101' via the shape memory element 200 is configured to lift the endometrial tissue ET. According to one example, the end effector 101' can be configured to cut the endometrial tissue ET in a direction that is substantially transverse to a direction (corresponding to the direction of arrows A3 and A4 of FIG. 3A) in which the end effector 101' via the shape memory element 200 is configured to lift the endometrial tissue ET. The end effector 101' can be configured to gather the endometrial tissue ET in a direction substantially transverse to or in another direction such as one that is in a range of between about 45 degrees and about 135 degrees, inclusive, of a surface the background tissue BT (e.g., the direction can transverse to the surface 150 or at an angle to the surface 150).

Although described with reference to the shape memory element 200, in alternative examples it is contemplated that the tissue removal tool could utilize other actuatable mechanisms for lifting the endometrial tissue ET that are not shape memory in configuration.

FIGS. 4A-6B show further examples of shape memory elements that can be utilized with the end effectors discussed herein. These and the shape memory element 200 of FIGS. 3A and 3B can be in an undeformed state when unactuated and in a deformed state when actuated. Examples of undeformed states are illustrated in FIGS. 3A, 4A, 5A and 6A. In the undeformed state, the shape memory element(s) can be disposed on a plane that is generally parallel to the plane defined the endometrial tissue and/or background tissue (e.g., the plane defined by a surface of the endometrial tissue and/or background tissue).

Examples of deformed states are illustrated in FIGS. 3B, 4B, 5B and 6B. In the deformed state, the shape memory element can wrap around the endometrial tissue to facilitate removal thereof by lifting (e.g., grasping, pulling, gathering, or the like). The shape memory element can deform to the deformed state when actuated. In the deformed state, the shape memory element can include at a least portion or feature thereof (e.g., a finger or slot) that can deform so as to be disposed along a plane non-parallel to the background tissue (for example, the slots and fingers of FIG. 6B can deform to form an angle of generally about 15-60 degrees, inclusive, relative to the plane along which the background tissue is disposed (such plane can be defined by a surface of the background tissue, for example).

Figure 4A:
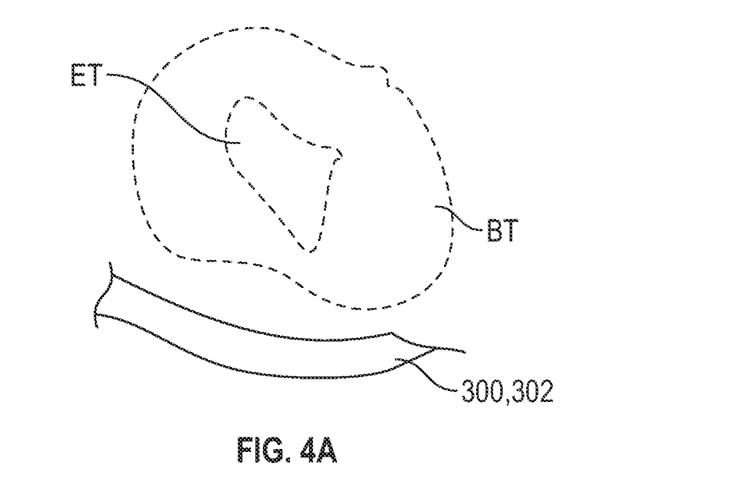
FIG. 4A shows a schematic view of another example of a shape memory element in an undeformed state positioned adjacent background tissue and endometrial tissue according to an example of the present application.
Figure 4B:
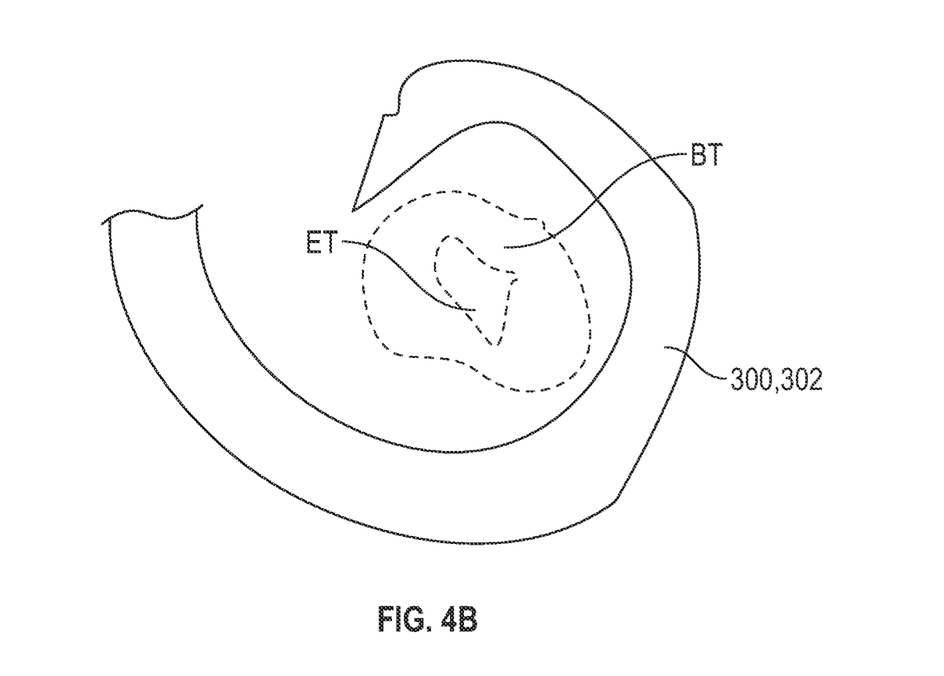
FIG. 4B shows a schematic view of the shape memory element of FIG. 4A in a deformed state and re-positioned relative to the background tissue and endometrial tissue according to an example of the present application.

FIG. 4A shows a schematic view of a shape memory element 300 comprising a finger 302 in an undeformed and unactuated state positioned adjacent background tissue BT and endometrial tissue ET. FIG. 4B shows a schematic view of the shape memory element 300 in an actuated and deformed state and positioned relative to the background tissue BT and endometrial tissue ET. FIGS. 4A and 4B are views from a lift direction of the shape memory element 300. Thus, as shown in FIG. 4B, the shape memory element 300 can be configured to deform when actuated to curl around or wrap around at least a portion of (or an entirety of) the endometrial tissue ET and/or background tissue BT. With this curling the shape memory element 300 can be configured as a hook, for example. Additionally, the curling of the shape memory element 300 can be substantially transverse (or at another acute or obtuse angle) relative to the lift direction (upward or downward into the page). Although illustrated in two-dimensions, the curling can be in three dimensions according to some examples. Thus, according to some examples the shape memory element 300 can curl in further directions into or out of the page of FIG. 4A that are not specifically illustrated. The curling can be along one or more surfaces of the endometrial tissue ET and/or background tissue BT, for example. The curling can be into or around the endometrial tissue ET and/or background tissue BT, for example. The curling can be along a plane non-parallel with the background tissue BT so the shape memory element 300 can be disposed along the plane non-parallel to the background tissue BT. Thus, for example, an angle of generally about 15-60 degrees, inclusive, can be formed between the shape memory element relative to the plane along which the background tissue BT is disposed (such plane can be defined by a surface of the background tissue).

Figure 5A:
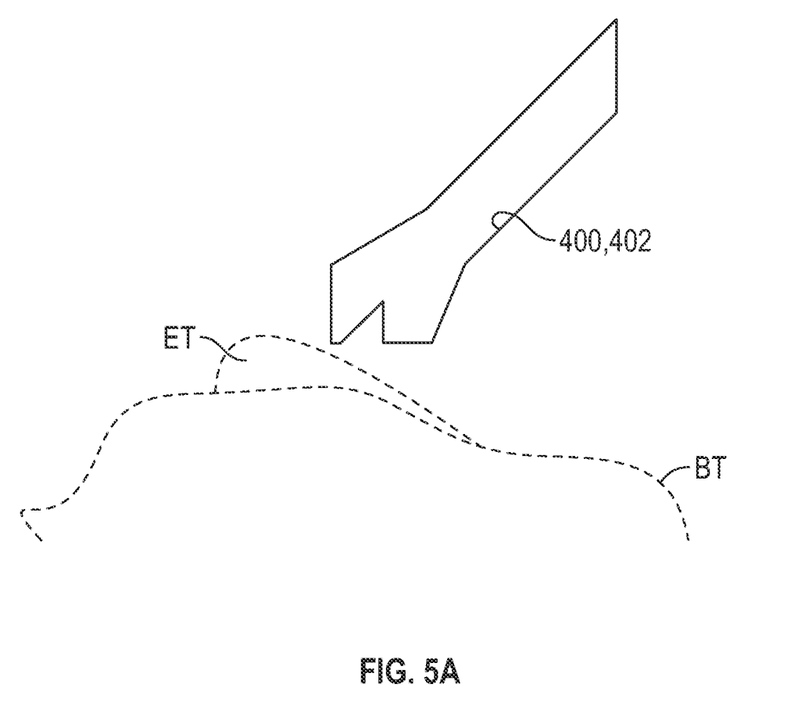
FIG. 5A shows a schematic view of another example of a shape memory element in ail undeformed state positioned adjacent background tissue and endometrial tissue according to an example of the present application.
Figure 5B:
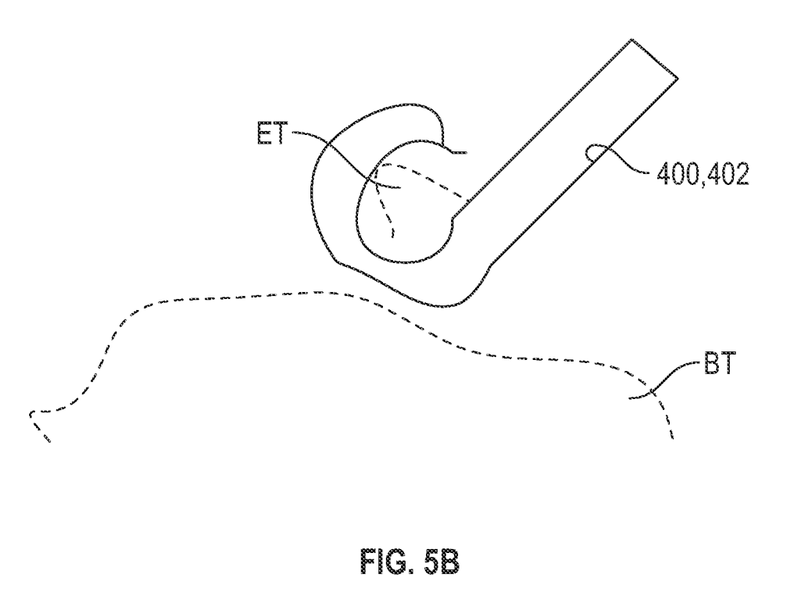
FIG. 5B shows a schematic view of the shape memory element of FIG. 5A in a deformed state grasping the endometrial tissue according to an example of the present application.

FIG. 5A shows a schematic view of a shape memory element 400 comprising a spatula 402 in an undeformed and unactuated state positioned adjacent background tissue BT and endometrial tissue ET. FIG. 5B shows a schematic view of the shape memory element 400 in an actuated and deformed state and grasping the endometrial tissue ET to remove it from the background tissue BT. As shown in FIG. 5B, the shape memory element 400 can be configured to deform when actuated to curl around or wrap around at least a portion of (or an entirety of) the endometrial tissue ET and/or background tissue BT. The shape memory element 400 can additionally be configured as the spatula 402 to dig into the endometrial tissue ET and/or background tissue BT in order to remove the endometrial tissue ET from the background tissue BT as shown in FIG. 5B. With the curling of FIG. 5B, the shape memory element 400 can be configured as a hook, for example. Additionally, the curling of the shape memory element 400 can be substantially transverse (or at another acute or obtuse angle) relative to the lift direction. Although illustrated in two-dimensions, the curling can be in three dimensions according to some examples. Thus, according to some examples the shape memory element 400 can curl in other directions such as into or out of the page of FIG. 5A that are not specifically illustrated. The curling can be along a plane non-parallel with the background tissue BT so the shape memory element 400 can be disposed along the plane non-parallel to the background tissue BT. Thus, for example, an angle of generally about 15-60 degrees, inclusive, can be formed between the shape memory element relative to the plane along which the background tissue BT is disposed (such plane can be defined by a surface of the background tissue).

Figure 6A:
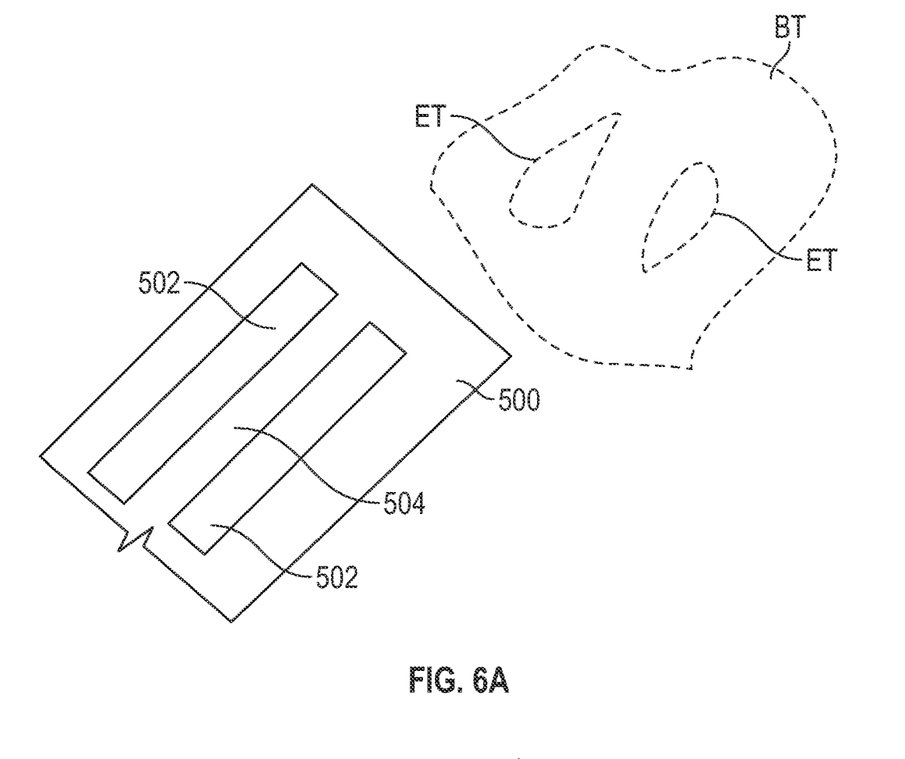
FIG. 6A shows a schematic view of another example of a shape memory element in an undeformed state positioned adjacent background tissue and endometrial tissue according to an example of the present application.
Figure 6B:
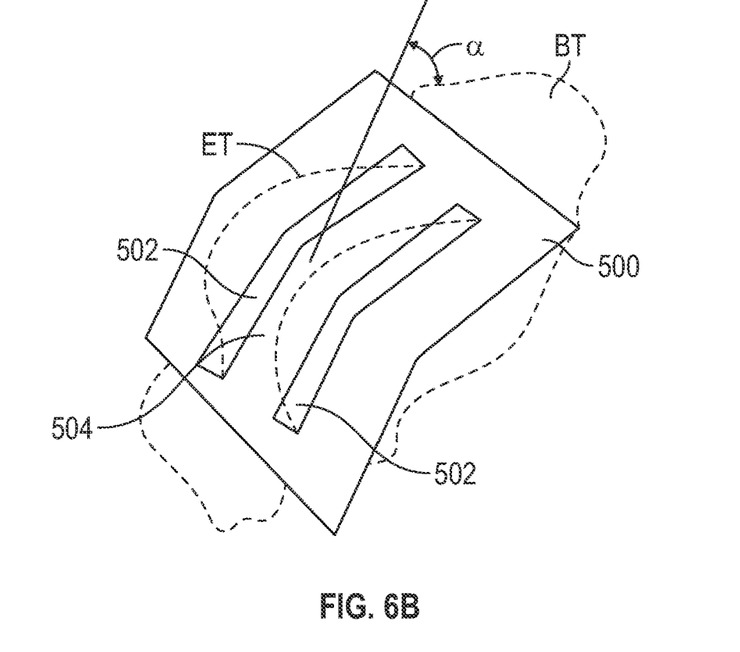
FIG. 6B shows a schematic view of the shape memory element of FIG. 6A in a deformed state grasping the endometrial tissue using fingers and slots according to an example of the present application.

FIG. 6A shows a schematic view of a shape memory element 500 comprising one or more slots 502 and one or more fingers 504 in an undeformed and unactuated state positioned adjacent background tissue BT and endometrial tissue ET. FIG. 6B shows a schematic view of the shape memory element 500 in an actuated and deformed state and grasping the endometrial tissue ET via the one or more slots 502 and one or more fingers 504 to remove the endometrial tissue ET from the background tissue BT. As shown in FIG. 6B, the shape memory element 500 can be configured to deform when actuated to become angled to grasp at least a portion of (or an entirety of) the endometrial tissue ET via passage of the endometrial tissue ET through the one or more slots 502. Put another way, the shape memory element 500 can be configured to deform to conform with the background tissue BT and can be configured to receive the endometrial tissue ET when deformed. Deformation of the shape memory element 500 can be configured to lift the endometrial tissue ET from the background tissue BT as shown in FIG. 6B. The deformation of the shape memory element 500 can be substantially transverse (or at another acute or obtuse angle) relative to the lift direction. As shown in FIG. 6B, the deformation (angling of the one or more fingers 504) can be along a plane non-parallel with the background tissue BT so the shape memory element 500 can be disposed along the plane non-parallel to the background tissue BT. Thus, for example, as shown in FIG. 6B an angle α of generally about 15-60 degrees, inclusive, can be formed between the shape memory element 600 relative to the plane along which the background tissue BT is disposed (such plane can be defined by a surface of the background tissue).

Various Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A tissue removal tool for treatment of endometrial tissue on a background tissue of a patient, the tissue removal tool comprising:
   a graspable portion;
   a shaft coupled to the graspable portion, the shaft having a proximal portion and a distal portion and configured to access an anatomic location of the endometrial tissue; and
   an end effector coupled to the distal portion of the shaft, wherein the end effector has a housing that defines a cavity, wherein the end effector includes a shape memory element that is configured to lift the endometrial tissue relative to the background tissue to a lifted position, and wherein the end effector is configured to cut the endometrial tissue from the background tissue with the endometrial tissue in the lifted position by receiving the endometrial tissue within the cavity of the end effector when lifted by the shape memory element, wherein the shape memory element is configured to deform when actuated to curl so as to wrap around at least a portion of the endometrial tissue.

2. The tissue removal tool of claim 1, wherein the end effector is moveable relative to the shaft to interface with the background tissue about the endometrial tissue.

3. The tissue removal tool of claim 2, wherein the end effector is moveable about at least an axis transverse to a longitudinal axis of the shaft.

4. The tissue removal tool of claim 1, wherein the end effector is configured to cut the endometrial tissue from the background tissue by receiving the endometrial tissue within a cavity of the end effector.

5. The tissue removal tool of claim 1, wherein the end effector is configured to cut in a plane that is substantially parallel with a surface of at least one of the background tissue or the endometrial tissue.

6. The tissue removal tool of claim 1, wherein the end effector is configured to lift the endometrial tissue by gathering.

7. The tissue removal tool of claim 1, wherein the end effector is configured to cut the endometrial tissue in a direction transverse to a direction in which the end effector is configured to lift the endometrial tissue.

8. The tissue removal tool of claim 1, further comprising a laparoscope defining a working channel that the shaft is inserted into.

9. The tissue removal tool of claim 1, wherein the curl is at an angle relative to a direction of the lift of the endometrial tissue.

10. The tissue removal tool of claim 1, wherein the shape memory element forms a hook when deformed to the curl.

11. A method of treating endometrial tissue at an anatomical location, the method comprising:
    guiding an end effector to the anatomical location;
    deforming a shape memory element to curl around at least a portion of the endometrial tissue;
    lifting the endometrial tissue with the shape memory element relative to a background tissue; and
    cutting the endometrial tissue from the background tissue with the end effector and with the endometrial tissue lifted from the background tissue.

12. The method of claim 11, wherein cutting the endometrial tissue is in a direction transverse to a direction of the lifting the endometrial tissue.

13. The method of claim 11, further comprising manipulating the end effector to interface with the background tissue.

14. The method of claim 11, wherein lifting the endometrial tissue comprises gathering the endometrial tissue with the deforming of the shape memory element.

15. The method of claim 11, wherein the curl is at an angle relative to a direction of the lifting of the endometrial tissue.

16. The method of claim 11, wherein the shape memory element forms a hook when deforming to the curl.

* * * * *

UNITED STATES PATENT AND TRADEMARK OFFICE
CERTIFICATE OF CORRECTION

| | | |
|---|---|---|
| PATENT NO. | : 11,819,244 B2 | Page 1 of 1 |
| APPLICATION NO. | : 17/099197 | |
| DATED | : November 21, 2023 | |
| INVENTOR(S) | : Holman et al. | |

It is certified that error appears in the above-identified patent and that said Letters Patent is hereby corrected as shown below:

On the Title Page

On page 2, in Column 2, under "U.S. Patent Documents", Line 9, delete "2019/0013371" and insert --2019/0133710-- therefor Signed and Sealed this
Fourth Day of February, 2025

Coke Morgan Stewart
*Acting Director of the United States Patent and Trademark Office*